(12) United States Patent
Hall

(10) Patent No.: US 9,109,488 B2
(45) Date of Patent: Aug. 18, 2015

(54) METHOD, SYSTEM, AND APPARATUS FOR DIAGNOSING AN EXHAUST AFTERTREATMENT COMPONENT

(71) Applicant: Cummins IP, Inc., Columbus, IN (US)

(72) Inventor: Tony James Hall, Lakewood, NY (US)

(73) Assignee: Cummins IP, Inc., Columbus, IN (US)

( * ) Notice: Subject to any disclaimer, the term of this patent is extended or adjusted under 35 U.S.C. 154(b) by 51 days.

(21) Appl. No.: 13/934,143

(22) Filed: Jul. 2, 2013

(65) Prior Publication Data

US 2014/0260201 A1 Sep. 18, 2014

Related U.S. Application Data

(60) Provisional application No. 61/788,546, filed on Mar. 15, 2013.

(51) Int. Cl.
*F01N 3/00* (2006.01)
*F01N 3/18* (2006.01)
(Continued)

(52) U.S. Cl.
CPC ..... *F01N 3/18* (2013.01); *F01N 3/208* (2013.01); *F01N 3/2066* (2013.01); *F01N 11/00* (2013.01); *F01N 2550/02* (2013.01);
(Continued)

(58) Field of Classification Search
USPC ............................ 60/274, 286, 297, 301, 303
See application file for complete search history.

(56) References Cited

U.S. PATENT DOCUMENTS 6,502,391 B1 * 1/2003 Hirota et al. .................... 60/288
7,067,319 B2 * 6/2006 Wills et al. ...................... 436/37
(Continued)

FOREIGN PATENT DOCUMENTS

DE 10 2012 207 247 3/2011

OTHER PUBLICATIONS

Air Resources Board, Field Evaluation of Heavy-Duty Diesel NOx, Control Strategies, Jan. 2013, http://www.arb.ca.gov/msprog/cihd/resources/reports/scrreportfinal.pdf.
(Continued)

*Primary Examiner* — Binh Q Tran
(74) *Attorney, Agent, or Firm* — Foley & Lardner LLP

(57) ABSTRACT

An apparatus includes an engine output module that determines an engine output power parameter for an engine. The apparatus includes an output power threshold module that determines if the engine output power parameter is below an output power threshold. The apparatus includes a NOx module that determines a nitrogen oxide ("NOx") efficiency of a selective catalytic reduction ("SCR") system in response to the output power threshold module determining that the determined engine output power parameter is below the output power threshold. The SCR system is in exhaust receiving communication with the engine. The apparatus includes a $NO_x$ threshold module that determines if the $NO_x$ efficiency is below a $NO_x$ efficiency threshold, and a $NO_x$ warning module that sends a $NO_x$ alarm signal in response to the $NO_x$ threshold module determining that the $NO_x$ efficiency is below the $NO_x$ efficiency threshold.

16 Claims, 7 Drawing Sheets

(51) Int. Cl.
*F01N 3/20* (2006.01)
*F01N 11/00* (2006.01)

(52) U.S. Cl.
CPC .... *F01N 2610/02* (2013.01); *F01N 2900/1402* (2013.01); *F01N 2900/1411* (2013.01); *F01N 2900/1621* (2013.01); *F01N 2900/1818* (2013.01); *Y02T 10/24* (2013.01); *Y02T 10/47* (2013.01)

(56) References Cited

U.S. PATENT DOCUMENTS

| | | | |
|---|---|---|---|
| 7,526,950 | B2 | 5/2009 | Van Nieuwstadt et al. |
| 7,610,750 | B2 | 11/2009 | Viola et al. |
| 8,091,342 | B2 * | 1/2012 | Perry et al. ............... 60/286 |
| 8,171,720 | B2 | 5/2012 | Wang et al. |
| 8,171,723 | B2 | 5/2012 | Hagimoto et al. |
| 8,424,289 | B2 * | 4/2013 | Narayanaswamy et al. .... 60/285 |
| 8,671,665 | B2 * | 3/2014 | Yasui .............. 60/286 |
| 2008/0178575 | A1 | 7/2008 | Shaikh et al. |
| 2008/0178656 | A1 | 7/2008 | Nieuwstadt et al. |
| 2009/0293451 | A1 | 12/2009 | Kesse |
| 2010/0083636 | A1 | 4/2010 | Wang et al. |
| 2011/0061372 | A1 | 3/2011 | Levijoki et al. |
| 2012/0192548 | A1 | 8/2012 | Shaikh et al. |

OTHER PUBLICATIONS

International Search Report and Written Opinion for International Application No. PCT/US2014/021798, dated Jun. 23, 2014, 11 pages.

* cited by examiner

METHOD, SYSTEM, AND APPARATUS FOR DIAGNOSING AN EXHAUST AFTERTREATMENT COMPONENT

CROSS-REFERENCE TO RELATED APPLICATION

This application claims the benefit of U.S. Provisional Patent Application No. 61/788,546, filed on Mar. 15, 2013, which is incorporated herein by reference.

FIELD

This invention relates to exhaust aftertreatment systems and more particularly relates to determining if diluted reductant is used in the exhaust aftertreatment systems.

BACKGROUND

Internal combustion engines emit gases and particulate that are considered a pollutant to the environment. The U.S. Environmental Protection Agency ("EPA") regulates what internal combustion engines are allowed to emit and has specific regulations for actions to happen if an engine exceeds the emissions regulations. One requirement for diesel engines and gasoline engines run lean is that a reductant fluid of a specific concentration is to be injected into the exhaust gas stream to reduce nitrogen oxide ("NOx") emissions. The EPA also requires that a vehicle be limited in speed if the reductant fluid is diluted above a specific level.

SUMMARY

An apparatus for diagnosing an exhaust aftertreatment component is disclosed. A system and method also perform the functions of the apparatus. The apparatus includes, in one embodiment, an engine output module that determines an engine output power parameter. The engine output power parameter is for an engine. The apparatus, in another embodiment, includes an output power threshold module that determines if the engine output power parameter is below an output power threshold. The apparatus also includes, in another embodiment, a NOx module that determines a nitrogen oxide ("NOx") efficiency of a selective catalytic reduction ("SCR") system in response to the output power threshold module determining that the determined engine output power parameter is below the output power threshold. The SCR system is in exhaust receiving communication with the engine. In another embodiment, the apparatus includes a NOx threshold module that determines if the NOx efficiency is below a NOx efficiency threshold, and a NOx warning module that sends a NOx alarm signal in response to the NOx threshold module determining that the NOx efficiency is below the NOx efficiency threshold.

In one embodiment, the apparatus includes a NOx change module and a NOx change threshold module. The NOx change module determines an amount of change in the NOx efficiency within a sampling window, and the NOx change threshold module determines if the amount of change in the NOx efficiency determined by the NOx change module exceeds a NOx efficiency change threshold. In the embodiment, the NOx warning module sends the NOx alarm signal in response to the NOx threshold module determining that the NOx efficiency is below the NOx efficiency threshold and the NOx change threshold module determining that the amount of change in the NOx efficiency exceeds the NOx efficiency change threshold.

In another embodiment, the NOx module determines the NOx efficiency while the determined engine output power parameter is within an engine output power range. The engine output power range is a range below the output power threshold, and the NOx change threshold module determines if the amount of change in the NOx efficiency exceeds the NOx efficiency change threshold using NOx efficiency determinations taken while the engine output power parameter is within the engine output power range. In another embodiment, the sampling window comprises a window of time or a number of consecutive samples.

In one embodiment, the engine output power parameter includes a level of exhaust flow of the engine and the output power threshold is an engine exhaust level threshold. In a further embodiment, the engine exhaust level threshold includes an engine exhaust flow level that is below 50 percent of a maximum exhaust flow level. In another embodiment, the engine output power parameter includes revolutions per minute ("RPM") of the engine and the output power threshold is an RPM threshold. In another embodiment, the engine output power parameter includes an engine power output level of the engine and the output power threshold is a level of engine power output. In another embodiment, the engine output power parameter includes a temperature of the engine and the output power threshold is a temperature threshold. In another embodiment, the engine output power parameter includes torque of the engine and the output power threshold is a torque threshold.

In one embodiment, the determined engine output power parameter includes an exponential weighted moving average of the determined engine output power parameter. In another embodiment, the engine output module determines the engine output power parameter in conjunction with a reductant tank refill event. In another embodiment, the engine output module determines the engine output power parameter at a sampling rate. In a further embodiment, the engine output module determines the engine output power parameter at the sampling rate during a period that the engine is operating within a set of engine operating parameters. In another embodiment, the apparatus includes a disable module that limits the engine to a low output in response to receiving the NOx alarm signal. In another embodiment, the NOx alarm signal comprises an FC3543 code for diluted reductant.

A system includes an SCR system in exhaust receiving communication with an engine, and a reductant dilution apparatus. The reductant dilution apparatus includes an engine output module that determines an engine output power parameter. The engine output power parameter is for the engine. The reductant dilution apparatus, in one embodiment, includes an output power threshold module that determines if the engine output power parameter is below an output power threshold. The reductant dilution apparatus includes, in another embodiment, a NOx module that determines a nitrogen oxide ("NOx") efficiency of the SCR system in response to the output power threshold module determining that the engine output power parameter is below the output power threshold. The reductant dilution apparatus includes, in another embodiment, a NOx threshold module that determines if the NOx efficiency is below a NOx efficiency threshold, and a NOx warning module that sends a NOx alarm signal in response to the NOx threshold module determining that the NOx efficiency is below the NOx efficiency threshold. In one embodiment, the system includes the engine. In another embodiment, the system includes a device powered by the engine.

A method for diagnosing an exhaust aftertreatment component includes determining an engine output power parameter for an engine and determining if the engine output power parameter is below an output power threshold. The method includes determining a NOx efficiency of an SCR system in response determining that the engine output power parameter is below the output power threshold. The SCR system is in exhaust receiving communication with the engine. The method includes determining if the NOx efficiency is below a NOx efficiency threshold, and sending a NOx alarm signal in response to determining that the NOx efficiency is below the NOx efficiency threshold.

In one embodiment, the method includes determining an amount of change in the NOx efficiency within a sampling window, and determining if the amount of change in the NOx efficiency exceeds a NOx efficiency change threshold. In the embodiment, sending the NOx alarm signal is in response to determining that the NOx efficiency is below the NOx efficiency threshold and determining that the amount of change in the NOx efficiency exceeds the NOx efficiency change threshold. In another embodiment, determining the NOx efficiency includes determining the NOx efficiency while the engine output power parameter is within an engine output power range. The engine output power range includes a range below the output power threshold, and determining if the amount of change in the NOx efficiency exceeds the NOx efficiency change threshold uses NOx efficiency determinations taken while the engine output power parameter is within the engine output power range. In another embodiment, the engine output power parameter comprises a level of exhaust flow of the engine and the output power threshold is an engine exhaust level threshold.

BRIEF DESCRIPTION OF THE DRAWINGS

In order that the advantages of the invention will be readily understood, a more particular description of the invention briefly described above will be rendered by reference to specific embodiments that are illustrated in the appended drawings. Understanding that these drawings depict only typical embodiments of the invention and are not therefore to be considered to be limiting of its scope, the invention will be described and explained with additional specificity and detail through the use of the accompanying drawings, in which.

DETAILED DESCRIPTION

Figure 1:
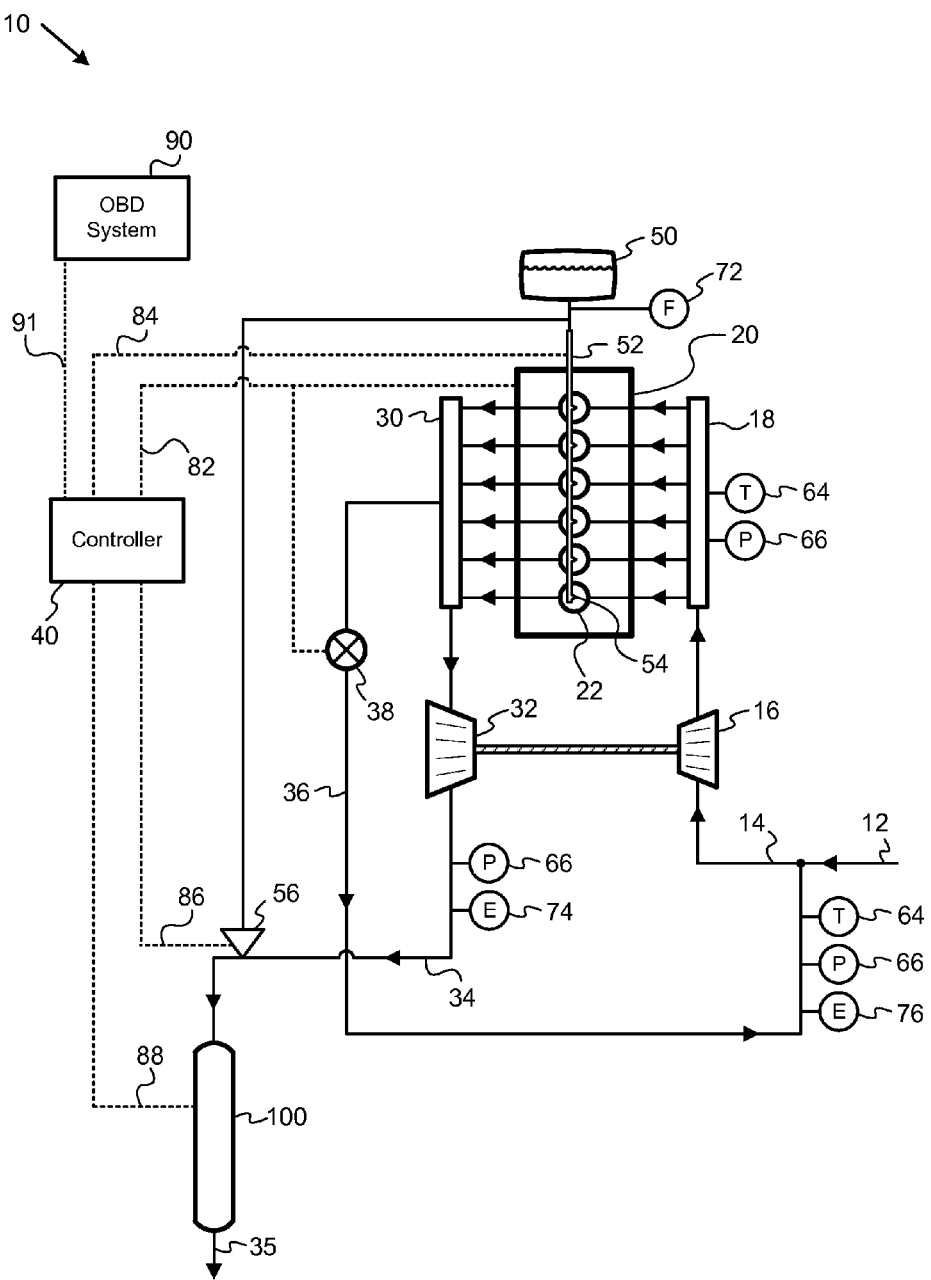
FIG. 1 is a schematic diagram of an engine system having an internal combustion engine and an exhaust aftertreatment system in accordance with one representative embodiment.

Reference throughout this specification to "one embodiment," "an embodiment," or similar language means that a particular feature, structure, or characteristic described in connection with the embodiment is included in at least one embodiment. Thus, appearances of the phrases "in one embodiment," "in an embodiment," and similar language throughout this specification may, but do not necessarily, all refer to the same embodiment, but mean "one or more but not all embodiments" unless expressly specified otherwise. The terms "including," "comprising," "having," and variations thereof mean "including but not limited to" unless expressly specified otherwise. An enumerated listing of items does not imply that any or all of the items are mutually exclusive and/or mutually inclusive, unless expressly specified otherwise. The terms "a," "an," and "the" also refer to "one or more" unless expressly specified otherwise.

Furthermore, the described features, advantages, and characteristics of the embodiments may be combined in any suitable manner. One skilled in the relevant art will recognize that the embodiments may be practiced without one or more of the specific features or advantages of a particular embodiment. In other instances, additional features and advantages may be recognized in certain embodiments that may not be present in all embodiments.

These features and advantages of the embodiments will become more fully apparent from the following description and appended claims, or may be learned by the practice of embodiments as set forth hereinafter. As will be appreciated by one skilled in the art, aspects of the present invention may be embodied as a system, method, and/or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module," or "system." Furthermore, aspects of the present invention may take the form of a computer program product embodied in one or more computer readable medium(s) having program code embodied thereon.

Many of the functional units described in this specification have been labeled as modules, in order to more particularly emphasize their implementation independence. For example, a module may be implemented as a hardware circuit comprising custom VLSI circuits or gate arrays, off-the-shelf semiconductors such as logic chips, transistors, or other discrete components. A module may also be implemented in programmable hardware devices such as field programmable gate arrays, programmable array logic, programmable logic devices or the like.

Modules may also be implemented in software for execution by various types of processors. An identified module of program code may, for instance, comprise one or more physical or logical blocks of computer instructions which may, for instance, be organized as an object, procedure, or function. Nevertheless, the executables of an identified module need not be physically located together, but may comprise disparate instructions stored in different locations which, when joined logically together, comprise the module and achieve the stated purpose for the module.

Indeed, a module of program code may be a single instruction, or many instructions, and may even be distributed over several different code segments, among different programs, and across several memory devices. Similarly, operational data may be identified and illustrated herein within modules, and may be embodied in any suitable form and organized within any suitable type of data structure. The operational data may be collected as a single data set, or may be distributed over different locations including over different storage devices, and may exist, at least partially, merely as electronic signals on a system or network. Where a module or portions of a module are implemented in software, the program code may be stored and/or propagated on in one or more computer readable medium(s).

The computer readable medium may be a tangible computer readable storage medium storing the program code. The computer readable storage medium may be, for example, but not limited to, an electronic, magnetic, optical, electromagnetic, infrared, holographic, micromechanical, or semiconductor system, apparatus, or device, or any suitable combination of the foregoing.

More specific examples of the computer readable storage medium may include but are not limited to a portable computer diskette, a hard disk, a random access memory ("RAM"), a read-only memory ("ROM"), an erasable programmable read-only memory ("EPROM" or Flash memory), a portable compact disc read-only memory ("CD-ROM"), a digital versatile disc ("DVD"), an optical storage device, a magnetic storage device, a holographic storage medium, a micromechanical storage device, or any suitable combination of the foregoing. In the context of this document, a computer readable storage medium may be any tangible medium that can contain, and/or store program code for use by and/or in connection with an instruction execution system, apparatus, or device.

The computer readable medium may also be a computer readable signal medium. A computer readable signal medium may include a propagated data signal with program code embodied therein, for example, in baseband or as part of a carrier wave. Such a propagated signal may take any of a variety of forms, including, but not limited to, electrical, electro-magnetic, magnetic, optical, or any suitable combination thereof. A computer readable signal medium may be any computer readable medium that is not a computer readable storage medium and that can communicate, propagate, or transport program code for use by or in connection with an instruction execution system, apparatus, or device. Program code embodied on a computer readable signal medium may be transmitted using any appropriate medium, including but not limited to wire-line, optical fiber, Radio Frequency ("RF"), or the like, or any suitable combination of the foregoing In one embodiment, the computer readable medium may comprise a combination of one or more computer readable storage mediums and one or more computer readable signal mediums. For example, program code may be both propagated as an electro-magnetic signal through a fiber optic cable for execution by a processor and stored on RAM storage device for execution by the processor.

Program code for carrying out operations for aspects of the present invention may be written in any combination of one or more programming languages, including an object oriented programming language such as Java, Smalltalk, C++, PHP or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network ("LAN") or a wide area network ("WAN"), or the connection may be made to an external computer (for example, through the Internet using an Internet Service Provider).

The computer program product may be shared, simultaneously serving multiple customers in a flexible, automated fashion. The computer program product may be standardized, requiring little customization and scalable, providing capacity on demand in a pay-as-you-go model. The computer program product may be stored on a shared file system accessible from one or more servers.

The computer program product may be integrated into a client, server and network environment by providing for the computer program product to coexist with applications, operating systems and network operating systems software and then installing the computer program product on the clients and servers in the environment where the computer program product will function.

In one embodiment software is identified on the clients and servers including the network operating system where the computer program product will be deployed that are required by the computer program product or that work in conjunction with the computer program product. This includes the network operating system that is software that enhances a basic operating system by adding networking features.

Furthermore, the described features, structures, or characteristics of the embodiments may be combined in any suitable manner. In the following description, numerous specific details are provided, such as examples of programming, software modules, user selections, network transactions, database queries, database structures, hardware modules, hardware circuits, hardware chips, etc., to provide a thorough understanding of embodiments. One skilled in the relevant art will recognize, however, that embodiments may be practiced without one or more of the specific details, or with other methods, components, materials, and so forth. In other instances, well-known structures, materials, or operations are not shown or described in detail to avoid obscuring aspects of an embodiment.

Aspects of the embodiments are described below with reference to schematic flowchart diagrams and/or schematic block diagrams of methods, apparatuses, systems, and computer program products according to embodiments of the invention. It will be understood that each block of the schematic flowchart diagrams and/or schematic block diagrams, and combinations of blocks in the schematic flowchart diagrams and/or schematic block diagrams, can be implemented by program code. The program code may be provided to a processor of a general purpose computer, special purpose computer, sequencer, or other programmable data processing apparatus to produce a machine, such that the instructions, which execute via the processor of the computer or other programmable data processing apparatus, create means for implementing the functions/acts specified in the schematic flowchart diagrams and/or schematic block diagrams block or blocks.

The program code may also be stored in a computer readable medium that can direct a computer, other programmable data processing apparatus, or other devices to function in a particular manner, such that the instructions stored in the computer readable medium produce an article of manufacture including instructions which implement the function/act specified in the schematic flowchart diagrams and/or schematic block diagrams block or blocks.

The program code may also be loaded onto a computer, other programmable data processing apparatus, or other devices to cause a series of operational steps to be performed on the computer, other programmable apparatus or other devices to produce a computer implemented process such that the program code which executed on the computer or other programmable apparatus provide processes for implementing the functions/acts specified in the flowchart and/or block diagram block or blocks.

The schematic flowchart diagrams and/or schematic block diagrams in the Figures illustrate the architecture, functionality, and operation of possible implementations of apparatuses, systems, methods and computer program products according to various embodiments of the present invention. In this regard, each block in the schematic flowchart diagrams and/or schematic block diagrams may represent a module, segment, or portion of code, which comprises one or more executable instructions of the program code for implementing the specified logical function(s).

It should also be noted that, in some alternative implementations, the functions noted in the block may occur out of the order noted in the Figures. For example, two blocks shown in succession may, in fact, be executed substantially concurrently, or the blocks may sometimes be executed in the reverse order, depending upon the functionality involved. Other steps and methods may be conceived that are equivalent in function, logic, or effect to one or more blocks, or portions thereof, of the illustrated Figures.

Although various arrow types and line types may be employed in the flowchart and/or block diagrams, they are understood not to limit the scope of the corresponding embodiments. Indeed, some arrows or other connectors may be used to indicate only the logical flow of the depicted embodiment. For instance, an arrow may indicate a waiting or monitoring period of unspecified duration between enumerated steps of the depicted embodiment. It will also be noted that each block of the block diagrams and/or flowchart diagrams, and combinations of blocks in the block diagrams and/or flowchart diagrams, can be implemented by special purpose hardware-based systems that perform the specified functions or acts, or combinations of special purpose hardware and program code.

FIG. 1 is a schematic diagram of an engine system 10 having an internal combustion engine and an exhaust aftertreatment system in accordance with one representative embodiment. The main components of the engine system 10 include an internal combustion engine 20 and an exhaust gas aftertreatment system 100 in exhaust gas-receiving communication with the engine 20. The internal combustion engine 20 can be a compression-ignited internal combustion engine, such as a diesel fueled engine, or a spark-ignited internal combustion engine, such as a gasoline fueled engine operated lean. On the intake side, the engine system 10 can include an air inlet 12, inlet piping 14, a turbocharger compressor 16, and an intake manifold 18. The intake manifold 18 includes an outlet operatively coupled to compression chambers 22 of the internal combustion engine 20 for introducing air into the compression chambers 22.

Within the internal combustion engine 20, air from the atmosphere is combined with fuel, and combusted, to power the engine. The fuel comes from the fuel tank 50 through a fuel delivery system including, in one embodiment, a fuel pump and common rail 52 to the fuel injectors 54, which inject fuel into the combustion chambers 22 of the engine 20. Fuel injection timing can be controlled by the controller 40 via a fuel injector control signal 84.

Combustion of the fuel and air in the compression chambers 22 produces exhaust gas that is operatively vented to an exhaust manifold 30. From the exhaust manifold 30, a portion of the exhaust gas may be used to power a turbocharger turbine 32. The turbocharger turbine 32 drives the turbocharger compressor 16, which may compress at least some of the air entering the air inlet 12 before directing it to the intake manifold 18 and into the compression chambers 22 of the engine 20.

For the purposes of altering the combustion properties of the engine 20, a portion of the exhaust gas may bypass the turbocharger turbine 32 and be re-circulated to the engine 20 via an exhaust gas recirculation ("EGR") line 36 and back to the inlet piping 14. In one embodiment, an EGR valve 38 is actuated to divert an amount of exhaust gas corresponding to a proportion set by a controller 40 via an EGR control signal.

The portion of the exhaust gas which is not re-circulated to the engine 20 via the EGR line 36 is destined for expulsion from the engine system 10 into the atmosphere. Thus, the exhaust gas stream flows from the exhaust manifold 30 or turbocharger turbine 32, through the exhaust piping 34, and through the exhaust gas aftertreatment system 100 prior to being vented into the atmosphere through tailpipe 35. The exhaust gas aftertreatment system 100 is configured to remove various chemical compounds and particulate emissions present in the exhaust gas received from the exhaust manifold 30. Specifically, the exhaust gas treated in the exhaust gas aftertreatment system 100 contains significantly fewer pollutants, such as unburned hydrocarbons, CO, diesel particulate matter, and $NO_x$, than untreated exhaust gas.

Various sensors, such as temperature sensors 64, pressure sensors 66, fuel sensor 72, exhaust gas flow sensors 74, 76 and the like, may be strategically disposed throughout the engine system 10 and may be in communication with the controller 40 to monitor operating conditions of the engine system 10. In one embodiment, the exhaust gas flow sensor 74 senses the rate at which the exhaust gas is flowing towards exhaust gas aftertreatment system 100.

Also, the engine system 10 may include an on-board diagnostic ("OBD") system 90 in electronic communication with the controller 40 via the control signal 91. Generally, the OBD system 90 is configured to alert a user (e.g., vehicle operator) of any operating condition faults monitored and triggered by the controller 40.

Figure 2:
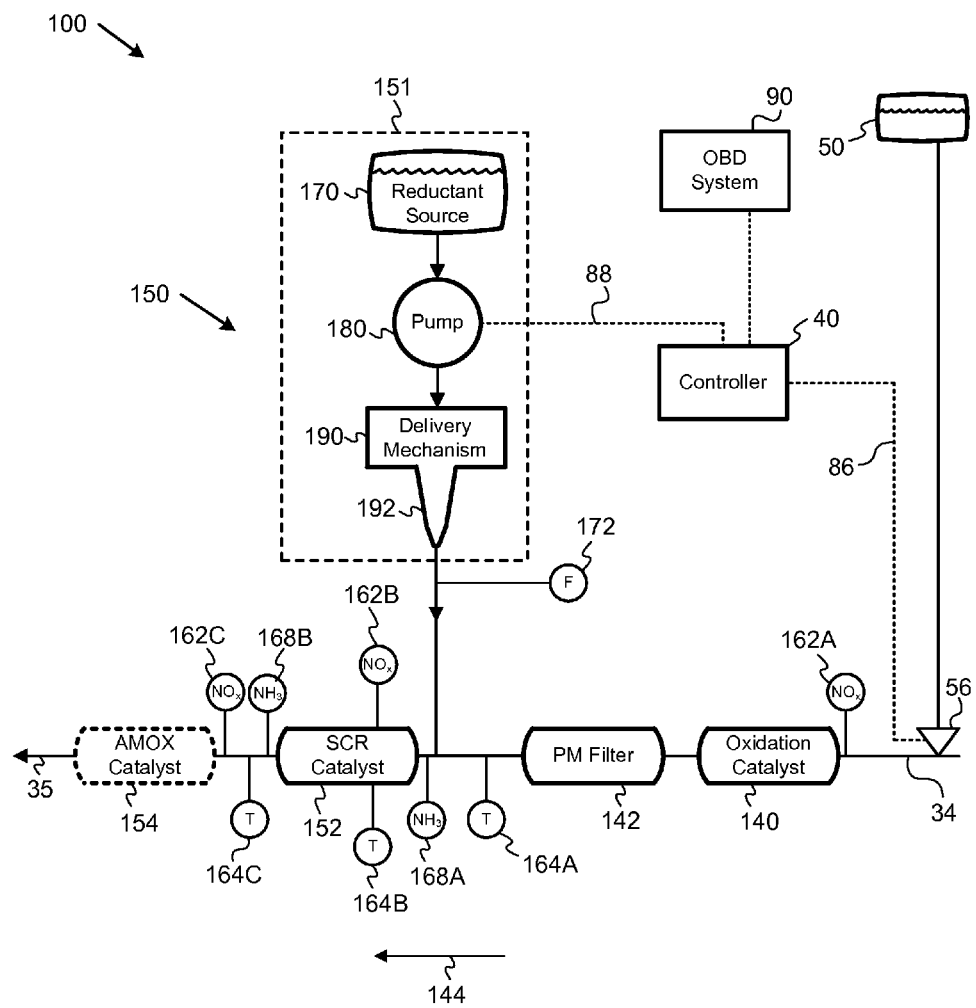
FIG. 2 is a schematic diagram of the exhaust aftertreatment system of FIG. 1 in accordance with one representative embodiment.

FIG. 2 is a schematic diagram of the exhaust aftertreatment system 100 of FIG. 1 in accordance with one representative embodiment. The exhaust gas aftertreatment system 100 includes the controller 40, the OBD system 90, an oxidation catalyst 140, a particulate matter ("PM") filter 142, an SCR system 150, and an optional ammonia oxidation ("AMOX") catalyst 154. The SCR system 150 has a reductant delivery system 151 and an SCR catalyst 152. The oxidation catalyst 140 can be any of various oxidation catalysts known in the art, such as a non-methane hydrocarbon catalyst. The PM filter 142 may be any of various particulate matter or other filters known in the art.

In an exhaust flow direction, as indicated by directional arrow 144, exhaust gas may flow from the exhaust piping 34, through the oxidation catalyst 140, through the PM filter 142, through the SCR catalyst 152, through the AMOX catalyst 154 if present, and then be expelled into the atmosphere through the tailpipe 35. Thus, in the illustrated embodiment the PM filter 142 is positioned downstream of the oxidation catalyst 140, the SCR catalyst 152 is positioned downstream of the PM filter 142, and the AMOX catalyst 154 is positioned downstream of the SCR catalyst 152. However, other arrangements of the components of the exhaust gas aftertreatment system 100 are also possible.

The oxidation catalyst 140 can have any of various flow-through designs known in the art, such as conventional diesel oxidation catalysts. Generally, the oxidation catalyst 140 is configured to oxidize at least some particulate matter, e.g., the soluble organic fraction of soot, in the exhaust and reduce unburned hydrocarbons and CO in the exhaust to less environmentally harmful compounds. For example, the oxidation catalyst 140 may sufficiently reduce the hydrocarbon and CO concentrations in the exhaust to meet the requisite emissions standards for those components of the exhaust gas. An indirect consequence of the oxidation capabilities of the oxidation catalyst 140 is the ability of the oxidation catalyst to oxidize nitrogen moNOxide ("NO") into $NO_2$. In this manner, the level of $NO_2$ exiting the oxidation catalyst 140 is equal to the $NO_2$ in the exhaust gas generated by the engine 20 plus the $NO_2$ converted from NO by the oxidation catalyst.

In addition to treating the hydrocarbon and CO concentrations in the exhaust gas, the oxidation catalyst 140 can also be used in the controlled regeneration of the PM filter 142 and the SCR catalyst 152. This can be accomplished through the injection, or dosing, of unburned hydrocarbons "UHC" into the exhaust gas upstream of the oxidation catalyst 140. Upon contact with the oxidation catalyst 140, the UHC undergoes an exothermic oxidation reaction which leads to an increase in the temperature of the exhaust gas exiting the oxidation catalyst 140 and subsequently entering the PM filter 142 and/or SCR catalyst 152. The amount of UHC added to the exhaust gas is selected to achieve the desired temperature increase or target controlled regeneration temperature.

The PM filter 142 can be any of various flow-through designs known in the art, including diesel particulate filters ("DPF"), and configured to reduce particulate matter concentrations, e.g., soot and ash, in the exhaust gas to meet requisite emission standards. In addition, the exhaust gas aftertreatment system 100 can further include a variety of sensors surrounding the PM filter 142 and which are electrically coupled to the controller 40.

The SCR system 150 includes a reductant delivery system 151 comprising a reductant source 170, pump 180 and delivery mechanism 190. The reductant source 170 can be a container or tank capable of retaining a reductant, such as, for example, ammonia ("$NH_3$"), urea, diesel fuel, or diesel oil. In one embodiment, the reductant is called diesel exhaust fluid ("DEF"). The reductant source 170 is in reductant supplying communication with the pump 180, which is configured to pump reductant from the reductant source to the delivery mechanism 190. The delivery mechanism 190 can include a reductant injector schematically shown at 192 positioned upstream of the SCR catalyst 152. The injector is selectively controllable to inject reductant directly into the exhaust gas stream prior to entering the SCR catalyst 152.

In some embodiments, the reductant can either be ammonia or urea, which decomposes to produce ammonia. The ammonia reacts with $NO_x$ in the presence of the SCR catalyst 152 to reduce the $NO_x$ to less harmful emissions, such as $N_2$ and $H_2O$. The $NO_x$ in the exhaust gas stream includes $NO_2$ and NO. Generally, both $NO_2$ and NO are reduced to $N_2$ and $H_2O$ through various chemical reactions driven by the catalytic elements of the SCR catalyst in the presence of $NH_3$. However, as discussed above, the chemical reduction of $NO_2$ to $N_2$ and $H_2O$ typically is the most efficient chemical reaction. Therefore, in general, the more $NO_2$ in the exhaust gas stream compared to NO, the more efficient the $NO_x$ reduction performed by the SCR catalyst. Accordingly, the ability of the oxidation catalyst 140 to convert NO to $NO_2$ directly affects the $NO_x$ reduction efficiency of the SCR system 150. Put another way, the $NO_x$ reduction efficiency of the SCR system 150 corresponds at least indirectly to the condition or performance of the oxidation catalyst 140. For example, a poorly performing (e.g., poorly conditioned) oxidation catalyst 140 may be more to blame for the presence of excess $NO_x$ exiting the tailpipe than any deficiencies associated with the SCR system 150. Therefore, the SCR system 150, in one embodiment, (and the associated $NO_x$ reduction performance of the SCR system 150) can act as a sensor to determine the condition of the oxidation catalyst 140.

Additionally, as discussed above, some PM filters oxidize NO to form $NO_2$ independent of the oxidation catalyst. Accordingly, a poorly performing (e.g., poorly conditioned) PM filter 142 may be more to blame for the presence of excess $NO_x$ exiting the tailpipe than any deficiencies associated with the SCR system 150. For this reason, the SCR system 150 can act as a sensor to determine the condition of the PM filter 142.

The SCR catalyst 152 can be any of various catalysts known in the art. For example, in some implementations, the SCR catalyst 152 is a vanadium-based catalyst, and in other implementations, the SCR catalyst is a zeolite-based catalyst, such as a Cu-Zeolite or a Fe-Zeolite catalyst. In one representative embodiment, the reductant is aqueous urea and the SCR catalyst 152 is a zeolite-based catalyst.

The AMOX catalyst 154 can be any of various flow-through catalysts configured to react with ammonia to produce mainly nitrogen. Generally, the AMOX catalyst 154 is utilized to remove ammonia that has slipped through or exited the SCR catalyst 152 without reacting with $NO_x$ in the exhaust. In certain instances, the exhaust gas aftertreatment system 100 can be operable with or without an AMOX catalyst 154. Further, although the AMOX catalyst 154 is shown as a separate unit from the SCR catalyst 152, in some implementations, the AMOX catalyst 154 can be integrated with the SCR catalyst, e.g., the AMOX catalyst 154 and the SCR catalyst 152 can be located within the same housing.

The embodiment of the exhaust aftertreatment system 100 illustrated in FIG. 2 incorporates multiple $NO_x$ sensors, which measure the amount (e.g., flow rate) of $NO_x$ in the exhaust gas throughout the exhaust treatment process. In some implementations, the exhaust aftertreatment system 100 may include one or more of an engine out $NO_x$ sensor 162A upstream of the oxidation catalyst 140 and downstream of the engine 20, an SCR mid-bed $NO_x$ sensor 162B embedded within the SCR catalyst 152, a tailpipe $NO_x$ sensor 162C downstream of the SCR catalyst 152 (and downstream of the AMOX catalyst 154 in some embodiments). In one embodiment, the mid-bed $NO_x$ sensor 162B measures $NO_x$ where the exhaust enters the SCR catalyst 152.

The exhaust aftertreatment system 100 can also utilize various other sensors for detecting corresponding characteristics of the exhaust gas or components. For example, the illustrated exhaust gas aftertreatment system 100 may include one or more of an SCR inlet temperature sensor 164A upstream of the SCR catalyst, an SCR mid-bed temperature sensor 164B embedded within the SCR catalyst, an SCR outlet temperature sensor 164C downstream of the SCR catalyst, an SCR inlet $NH_3$ sensor 168A upstream of the SCR catalyst 152, and an SCR outlet $NH_3$ sensor 168B located downstream of the SCR catalyst, and the like. In some cases, a $NO_x$ sensor and an $NH_3$ sensor may be combined into a dual ammonia-$NO_x$ sensor (not shown). The various sensors may be in electrical communication with the controller 40 to allow the controller monitor the operating conditions of the exhaust gas aftertreatment system 100 of the engine system 10.

Although the exhaust gas aftertreatment system 100 shown includes one of an oxidation catalyst 140, PM filter 142, SCR catalyst 152, and AMOX catalyst 154 positioned in specific locations relative to each other along the exhaust flow path, in other embodiments, the exhaust gas aftertreatment system 100 may include more than one of any of the various catalysts positioned in any of various positions relative to each other along the exhaust flow path as desired. Further, although the oxidation catalyst 140 and AMOX catalyst 154 are non-selective catalysts, in some embodiments, the oxidation and AMOX catalysts 140, 154 can be selective catalysts.

The controller 40 controls the operation of the engine system 10 and associated sub-systems, such as the internal combustion engine 20 and the exhaust gas aftertreatment system 100. The controller 40 is depicted in FIGS. 1 and 2 as a single physical unit, but can include two or more physically separated units or components in some embodiments if desired. Generally, the controller 40 receives multiple inputs, processes the inputs, and transmits multiple outputs. The multiple inputs may include sensed measurements from the sensors and various user inputs. The inputs are processed by the controller 40 using various algorithms, stored data, and other inputs to update the stored data and/or generate output values. The generated output values and/or commands are transmitted to other components of the controller and/or to one or more elements of the engine system 10 to control the system to achieve desired results, and more specifically, achieve desired exhaust gas emissions.

For example, the operating conditions of the internal combustion engine 20 and the exhaust gas aftertreatment system 100 can be ascertained from any of the sensors or from the controller's 40 commands to the engine regarding the fraction of exhaust gas recirculation, injection timing, and the like. In one embodiment, information is gathered regarding, for example, fuel rate, engine speed, engine load, the timing at which fuel injection timing is advanced or retarded ("SOT," or start of injection), the fraction of exhaust gas recirculation, driving conditions, exhaust flow rate, the amount of $O_2$, $NO_x$ (e.g., "$NO_2$" and "NO"), and $NH_3$ in the exhaust gas, and exhaust gas temperatures and pressures at various locations within the exhaust gas aftertreatment system 100.

The controller 40 includes various modules for controlling the operation of the engine system 10. For example, the controller 40 includes one or more modules for controlling the operation of the internal combustion engine 20. The controller 40 further includes one or more modules for controlling the operation and regeneration of the SCR system 150. Additionally, the controller 40 include one or more modules for diagnosing the performance or conditions of one or more components of the exhaust gas aftertreatment system 100, and reporting the diagnosed performance or conditions to the OBD system 90.

As is known in the art, the controller 40 and its various modular components may comprise processor, memory, and interface modules that may be fabricated of semiconductor gates on one or more semiconductor substrates. Each semiconductor substrate may be packaged in one or more semiconductor devices mounted on circuit cards. Connections between the modules may be through semiconductor metal layers, substrate-to-substrate wiring, or circuit card traces or wires connecting the semiconductor devices.

A potential problem with the SCR system 150 is that the reductant source 170 may include reductant that is diluted, for example with water. Diluted reductant typically causes the SCR system 150 to operate less efficiently. Typically, diluted reductant causes the $NO_x$ efficiency to be reduced. Currently, diluted reductant is difficult to distinguish from other failures in the SCR system 150.

Figure 3:
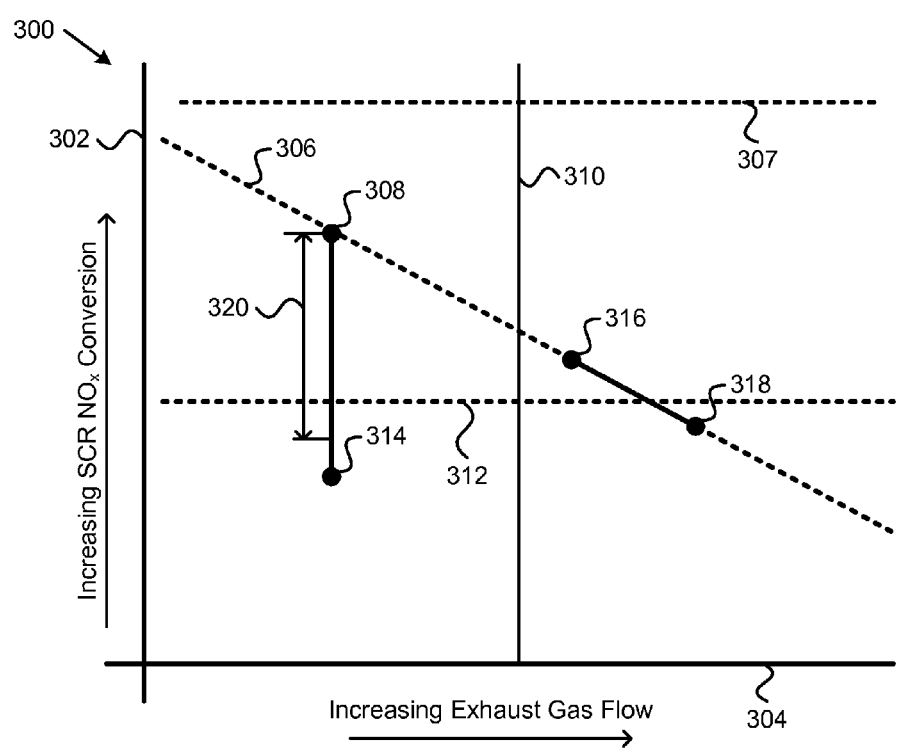
FIG. 3 is a diagram of $NO_x$ efficiency versus exhaust gas flow.

FIG. 3 is a diagram 300 of $NO_x$ efficiency versus exhaust gas flow. The vertical axis 302 represents increasing SCR $NO_x$ conversion (i.e. increasing $NO_x$ efficiency) and the horizontal axis 304 represents increasing exhaust gas flow. The sloping line 306 represents a typical $NO_x$ conversion efficiency for a particular field aged an SCR system 150. The sloping line 306 may represent an aged SCR system 150 that is nearing end-of-life. The horizontal line 307 at the top of the diagram represents a new SCR system 150. A first operating point 308 represents an operating condition for the engine 20 where the exhaust gas output is relatively low and is below an engine exhaust level threshold 310. The diagram 300 also includes a line that represents a $NO_x$ efficiency threshold 312. Note that the sloping line 306 for the field aged SCR system 150 extends below the $NO_x$ efficiency threshold 312 for high exhaust gas flow conditions. The second operating point 314 indicates a condition where the exhaust gas flow is the same as for the first operating point 308, but is below the $NO_x$ efficiency threshold 312. The second operating point 314 may indicate a condition where the reductant is diluted.

Note that for higher exhaust flow condition, a third operating point 316 may be above the $NO_x$ efficiency threshold 312, but a fourth operating point 318 for an even higher exhaust flow condition for the SCR system 150 is below the $NO_x$ efficiency threshold 312. In a condition where the controller 40 samples $NO_x$ efficiency, the third operating point 316 may be a sampled point and may indicate that the SCR system 150 is operating normally and then at the next sampling time, exhaust gas flow may be increased so that the fourth operating point 318 is the next sampling point and is below the $NO_x$ efficiency threshold 312. The controller 40 may then signal that the SCR system 150 is operating below the $NO_x$ efficiency threshold 312. Thus where exhaust gas flow is not accounted for, and aged SCR system 150 may not be able to distinguish between a condition of a diluted reductant and a condition where the exhaust gas flow is high. Other failures in the SCR system 150 may also cause the SCR system 150 operate below the $NO_x$ efficiency threshold 312 and begin may not be distinguished from the condition of diluted reductant.

One representative embodiment of an apparatus to diagnose a diluted reductant condition may include a requirement sampling $NO_x$ efficiency at a low exhaust gas flow condition. In another embodiment, the apparatus may include a combination of a $NO_x$ efficiency below the $NO_x$ efficiency threshold 312 and a step change that is a decrease in $NO_x$ efficiency greater than a certain amount. A step change is shown in the diagram 300 that may indicate a $NO_x$ efficiency change threshold 320.

While FIG. 3 indicates a correlation between exhaust gas flow and $NO_x$ efficiency for an SCR system 150, other measured parameters for the engine 20 may also include a correlation between $NO_x$ efficiency for the SCR system 150 and another engine output power parameter, such as an amount of power output by the engine 20, torque, engine temperature, engine speed, and the like. One of skill in the art will recognize other engine power parameters that correlate with $NO_x$ efficiency for an SCR system 150 that has a characteristic of decreased $NO_x$ efficiency for higher engine output power parameters.

Figure 4:
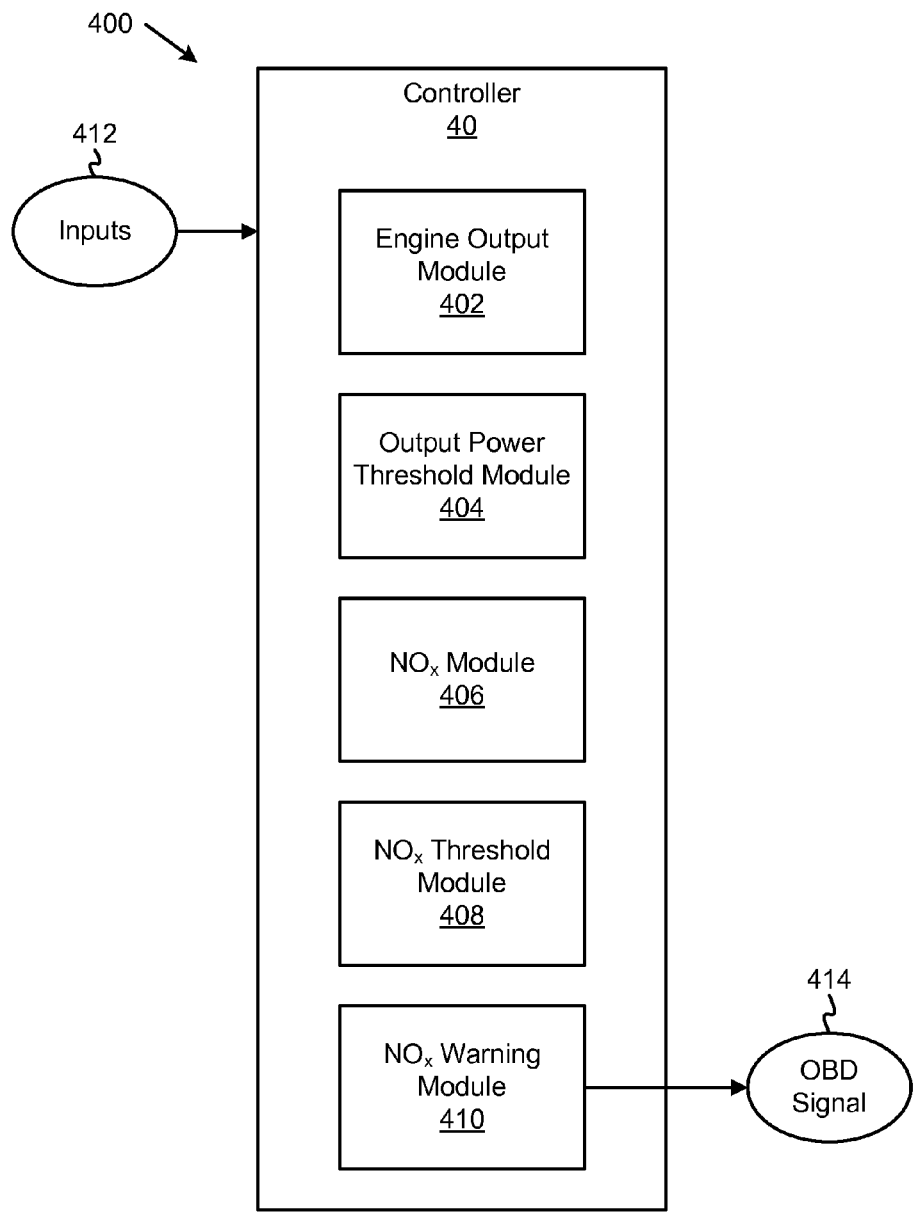
FIG. 4 is a schematic block diagram of an apparatus with one embodiment of a controller of the engine system of FIG. 1 in accordance with one representative embodiment.

FIG. 4 is a schematic block diagram of an apparatus 400 with one embodiment of a controller 40 of the engine system 10 of FIG. 1 in accordance with one representative embodiment. The apparatus 400 includes a controller 40 with an engine output module 402, an output power threshold module 404, a $NO_x$ module 406, a $NO_x$ threshold module 408, and a $NO_x$ warning module 410, which are described below.

In one embodiment, the apparatus 400 includes an engine output module 402 that determines an engine output power parameter for the engine 20. The engine output power parameter, in one embodiment, is a determination of a level of exhaust flow of the engine 20. The engine exhaust flow level may be determined from a measurement from the exhaust gas flow sensor 74 as the exhaust gas travels through the exhaust piping 34. In another embodiment, the engine output power parameter includes revolutions per minute ("RPM" or engine speed) of the engine 20. An RPM sensor may be used to determine RPM of the engine 20. In another embodiment, the engine output power parameter includes an engine power output level of the engine 20. For example, the engine power output level may be in horsepower or other suitable power unit. Output power may be determined by the controller 40 by measuring various engine parameters indicative of power. In another embodiment, the engine output power parameter includes a temperature of the engine 20. For example, temperature sensors 64 for the engine 20 and related parts may be used to determine temperature of the engine 20. In another embodiment, the engine output power parameter includes torque of the engine 20. One or more sensors may be used to determine torque of the engine 20.

In one embodiment, the engine output module 402 determines the engine output power parameter at a sampling rate. The sampling rate may be constant or may be tied to other engine operating parameters, such as operating at a certain output power level, a certain RPM, etc. In one embodiment, the determined engine output power parameter includes an exponential weighted moving average ("EWMA") of the determined engine output power parameter. Using an EWMA may allow measurements or samples that are affected by transients or other abnormal conditions to be averaged in with other measurements and/or samples to avoid false triggers. As used herein, the engine output power parameter may be a single measurement or may be an average of several samples or measurements using an EWMA or other averaging method. In another embodiment, the engine output module 402 determines the engine output power parameter at the sampling rate during a period that the engine is operating within a set of engine operating parameters. For example, the engine operating parameters may exclude extreme conditions or conditions such as idling, high output associated with a steep incline, startup, etc. For instance, certain systems may not be operating during startup or other times and the engine output module 402 may sample when the various systems are operational. In one embodiment, the engine output module 402 may sample or determine the engine output power parameter after a reductant tank refill event.

In one embodiment, the apparatus 400 includes an output power threshold module 404 that determines if the measured engine output power parameter is below an output power threshold. In one embodiment, the output power threshold is an engine exhaust level threshold 310. For example, the engine exhaust level threshold 310 may be an engine exhaust flow level that is below 50 percent of a maximum exhaust flow level. In an embodiment, where the engine output power parameter is revolutions per minute ("RPM") of the engine 20, the output power threshold may be an RPM threshold. In another embodiment where the engine output power parameter is an engine power output level of the engine 20, the output power threshold may be a level of engine power output. Where the engine output power parameter is a temperature of the engine 20, the output power threshold may be a temperature threshold. Where the engine output power parameter is torque of the engine 20, the output power threshold may be a torque threshold. One of skill in the art will recognize other engine output power parameters and appropriate thresholds.

In one embodiment, the apparatus 400 includes a $NO_x$ module 406 that determines a $NO_x$ efficiency of the SCR system 150 in response to the output power threshold module 404 determining that the engine output power parameter is below the output power threshold. In another embodiment, the apparatus 400 includes a $NO_x$ threshold module 408 that determines if the $NO_x$ efficiency is below a $NO_x$ efficiency threshold 312. For example, when exhaust gas flow is the output power parameter, the $NO_x$ module 406 may determine $NO_x$ efficiency for various sampling points that occur when the output power threshold module 404 determines that the exhaust gas flow level is below and engine exhaust level threshold 310. The $NO_x$ threshold module 408 may determine that the $NO_x$ efficiency is above the $NO_x$ efficiency threshold 312, for example when the reductant is not diluted. Other sampling points that occur while the engine 20 is operating at an exhaust gas flow level above the engine exhaust level threshold 310 may be ignored or may be used for a different purpose by the controller 40.

For another sampling point where the output power threshold module 404 determines that the engine output power parameter is below the output power threshold, the $NO_x$ threshold module 408 may determine that the $NO_x$ efficiency determined by the $NO_x$ module 406 is below the $NO_x$ efficiency threshold 312, for example while diluted reductant is in the SCR system 150. While the engine output power parameter is below the output power threshold, one typical condition where the SCR system 150 will have a $NO_x$ efficiency above the $NO_x$ efficiency threshold 312 and then have a $NO_x$ efficiency below the $NO_x$ efficiency threshold 312 is when the reductant source 170 (i.e. a tank) becomes diluted when refilled. Other failures may also cause this condition as well. Other sensors may be used to detect other failures to possibly distinguish between diluted reductant and other failures. In one embodiment, the engine output module 402 determines or samples the engine output power parameter after a reductant tank refill event and when the engine output power parameter is below the output power threshold. The $NO_x$ threshold module 408 may then compare $NO_x$ efficiencies after another reductant refill event, which may correlate $NO_x$ efficiencies below the $NO_x$ efficiency threshold 312 to a reductant tank refill event. This sampling after a refill event may increase the likelihood that a $NO_x$ efficiency below the $NO_x$ efficiency threshold 312 is related to diluted reductant.

The apparatus 400, in one embodiment, includes a $NO_x$ warning module 410 that sends a $NO_x$ alarm signal in response to the $NO_x$ threshold module 408 determining that the $NO_x$ efficiency is below the $NO_x$ efficiency threshold 312. For example, the $NO_x$ alarm signal may be an FC3543 code for diluted reductant, as mandated by the EPA. The $NO_x$ warning module may send the $NO_x$ alarm signal to the controller 40. In another embodiment, the $NO_x$ warning module 410 sends the $NO_x$ alarm signal to the OBD system 90 as an OBD signal 414 to display a warning on a display panel. In another embodiment, the $NO_x$ alarm signal is sent over a computer network, such as a wireless or cellular network, to a server or other computer. One of skill in the art will recognize other $NO_x$ alarm signals and destinations.

Figure 5:
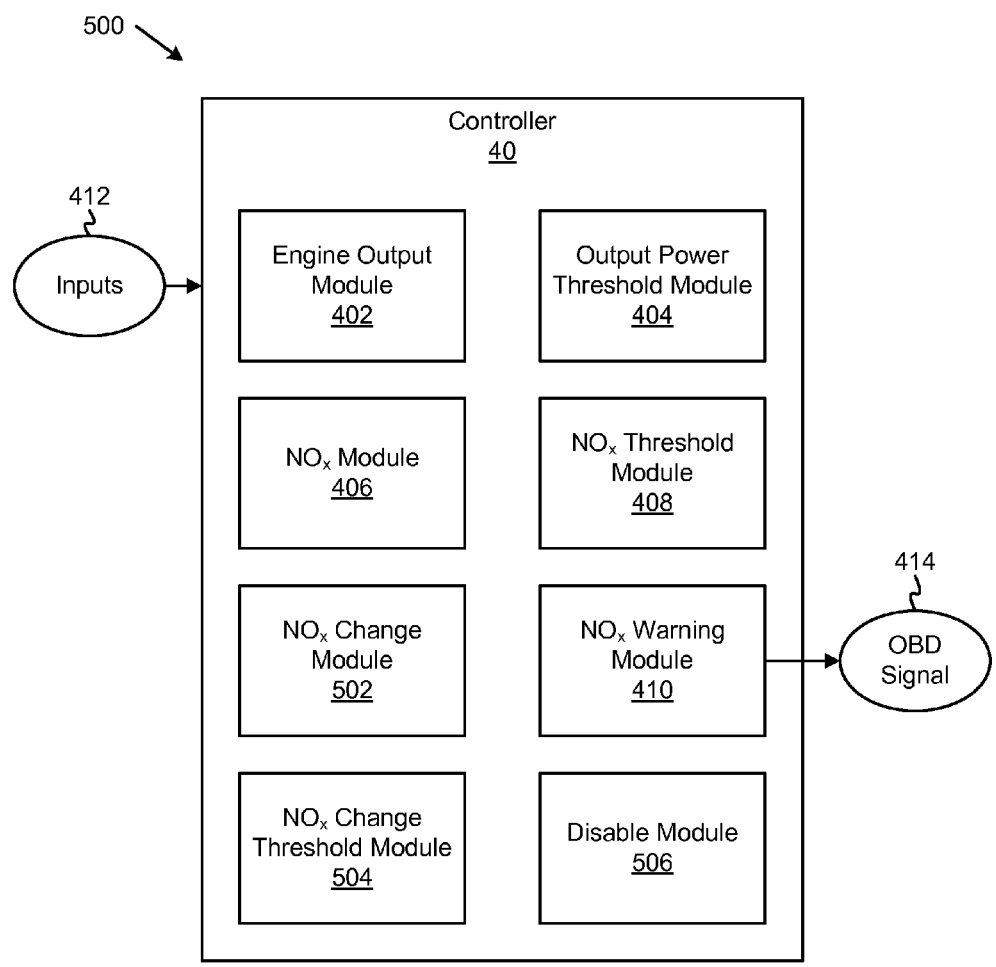
FIG. 5 is a schematic block diagram of an alternate embodiment of an apparatus with another embodiment of a controller of the engine system of FIG. 1 in accordance with one representative embodiment.

FIG. 5 is a schematic block diagram of an alternate embodiment of an apparatus 500 with another embodiment of a controller 40 of the engine system of FIG. 1 in accordance with one representative embodiment. The apparatus 500 includes a controller 40 with an engine output module 402, an output power threshold module 404, a $NO_x$ module 406, a $NO_x$ threshold module 408, and a $NO_x$ warning module 410, which are substantially similar to those described in relation to the apparatus 400 of FIG. 4. The apparatus 500, in various embodiments, may also include a controller 40 with a $NO_x$ change module 502, a $NO_x$ change threshold module 504, and a disable module 506, which are described below.

In one embodiment, the apparatus 500 includes a $NO_x$ change module 502 and a $NO_x$ change threshold module 504. The $NO_x$ change module 502 determines an amount of change in the $NO_x$ efficiency within a sampling window and the $NO_x$ change threshold module 504 determines if the amount of change in the $NO_x$ efficiency determined by the $NO_x$ change module exceeds a $NO_x$ efficiency change threshold 320. In one example, the $NO_x$ warning module 410 sends the $NO_x$ alarm signal in response to the $NO_x$ threshold module 408 determining that the $NO_x$ efficiency is below the $NO_x$ efficiency threshold and the $NO_x$ change threshold module 504 determining that the amount of change in the $NO_x$ efficiency exceeds the $NO_x$ efficiency change threshold 320. In the example, a $NO_x$ efficiency change exceeding the $NO_x$ efficiency change threshold 320 may be related to an engine condition that may be unrelated to detecting diluted reductant and triggering the $NO_x$ warning module 410 to send the $NO_x$ alarm signal may be more accurate when both the $NO_x$ efficiency threshold 312 and the $NO_x$ efficiency change threshold 320 are exceeded. In another example, the $NO_x$ warning module 410 sends the $NO_x$ alarm signal in response to either the $NO_x$ threshold module 408 determining that the $NO_x$ efficiency is below the $NO_x$ efficiency threshold or the $NO_x$ change threshold module 504 determining that the amount of change in the $NO_x$ efficiency exceeds the $NO_x$ efficiency change threshold 320.

In one embodiment, the sampling window is a window of time. In another embodiment, the sampling window is a number of consecutive samples. In another embodiment, the $NO_x$ module 406 determines the $NO_x$ efficiency while the engine output power parameter is within an engine output power range. The engine output power range may include a range that is below the output power threshold. For example, the $NO_x$ module 406 may determine the $NO_x$ efficiency at several operating points within the engine output power range while the reductant is not diluted. The $NO_x$ module 406 may determine a $NO_x$ efficiency while the engine 20 is operating in the engine output power range and the $NO_x$ change threshold module 504 may then determine if the amount of change in the $NO_x$ efficiency exceeds the $NO_x$ efficiency change threshold 320 using $NO_x$ efficiency determinations taken while the engine output power parameter is within the engine output power range.

In one embodiment, the apparatus 500 includes a disable module 506 that limits the engine 20 to a low output in response to receiving the $NO_x$ alarm signal. For example, the disable module 506 may limit a vehicle powered by the engine 20 to a speed of 5 miles per hour. In another embodiment, the disable module 506 may not allow the engine 20 to start after receiving the $NO_x$ alarm signal and then being turned off. The disable module 506, in one embodiment, may take action to comply with requirements of the EPA. In another embodiment, the disable module 506 may allow a certain number of $NO_x$ alarm signals before disabling the vehicle. For example, the $NO_x$ warning module 410 may send the $NO_x$ alarm signal in the form of an OBD signal 414 to be displayed to a user of the engine 20 and the disable module 506 may not act on the first $NO_x$ alarm signal and then the disable module 506 may limit the vehicle on a second $NO_x$ alarm signal. In other embodiments, additional $NO_x$ alarm signals may be ignored by the disable module 506 and/or controller 40 before the disable module 506 limits the vehicle. One of skill in the art will recognize other ways to for the disable module 506 to limit a vehicle or device powered by the engine 20.

Figure 6:
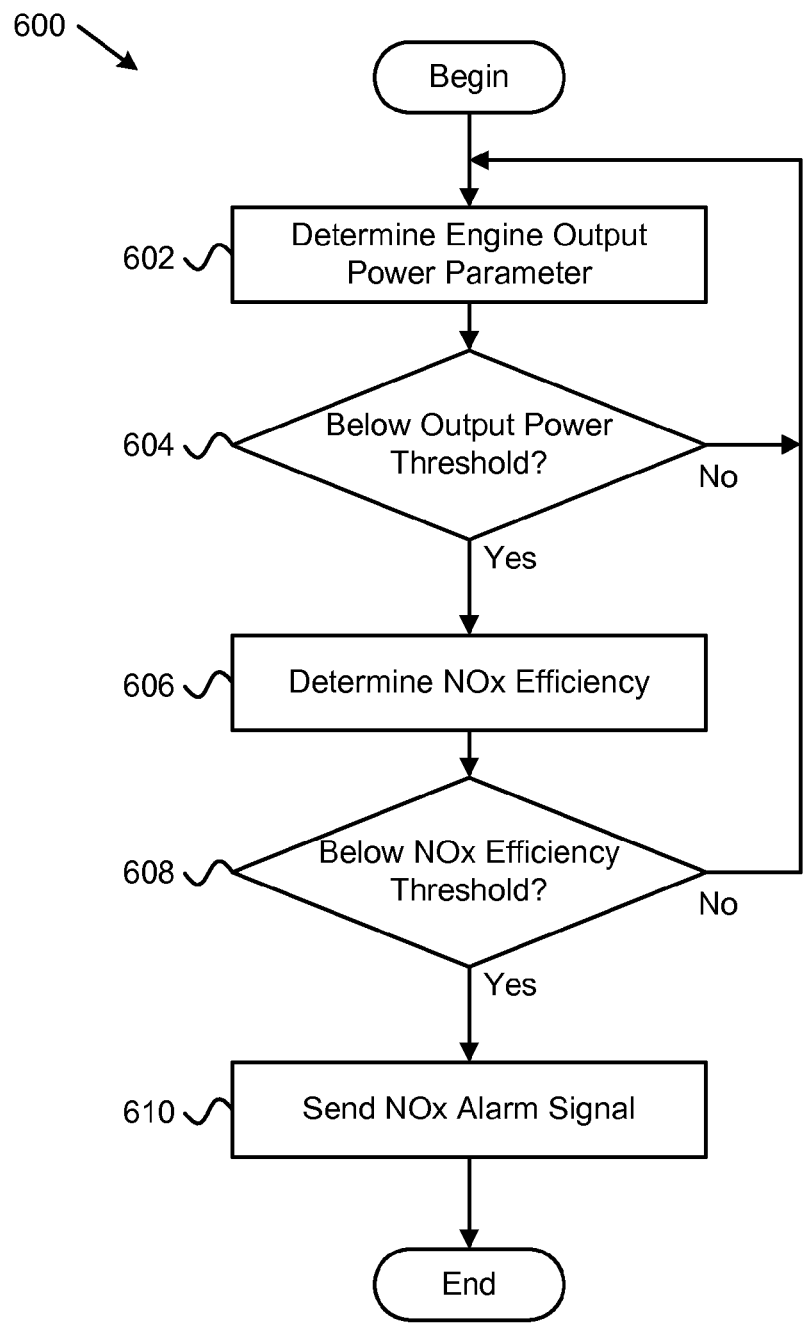
FIG. 6 is a schematic block diagram illustrating one embodiment of a method for diagnosing an exhaust aftertreatment in accordance with one representative embodiment.

FIG. 6 is a schematic block diagram illustrating one embodiment of a method 600 for diagnosing an exhaust aftertreatment in accordance with one representative embodiment. The method 600 begins and determines 602 an engine output power parameter for the engine 20 and determines 604 if the engine output power parameter is below an output power threshold. If the method 600 determines 604 that the engine output power parameter is not below the output power threshold, the method 600 returns and again determines 602 an engine output power parameter. If the method 600 determines 604 that the engine output power parameter is below the output power threshold, the method determines 606 a $NO_x$ efficiency of the SCR system 150. The method 600 determines 608 if the $NO_x$ efficiency is below a $NO_x$ efficiency threshold 312. If the method 600 determines 608 that the $NO_x$ efficiency is not below a $NO_x$ efficiency threshold 312, the method 600 returns and again determines 602 an engine output power parameter. If the method 600 determines 608 that the $NO_x$ efficiency is below a $NO_x$ efficiency threshold 312, the method 600 sends 610 a $NO_x$ alarm signal, and the method 600 ends. One or more of the engine output module 402, the output power threshold module 404, the $NO_x$ module 406, the $NO_x$ threshold module 408, and the $NO_x$ warning module 410 may be employed to perform the steps of the method 600.

Figure 7:
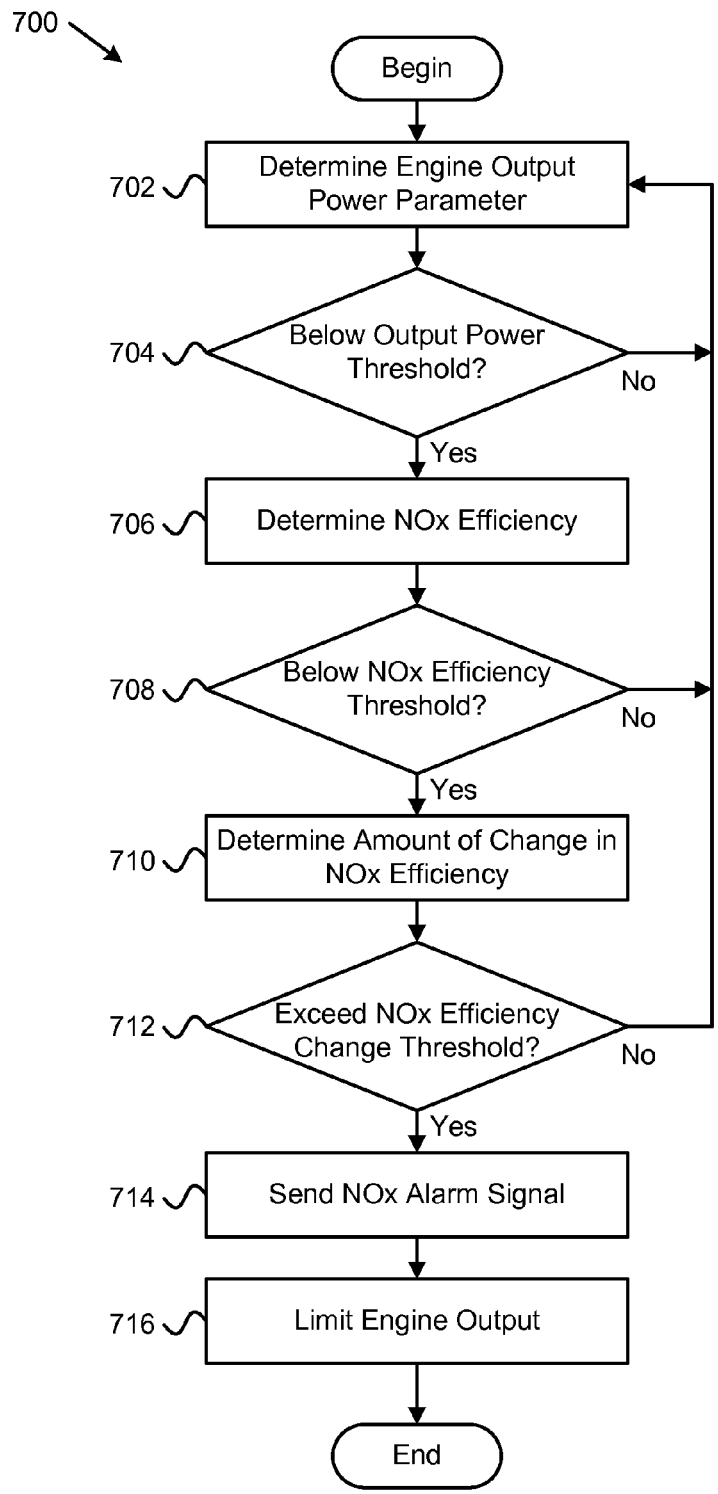
FIG. 7 is a schematic block diagram illustrating another embodiment of a method for diagnosing an exhaust aftertreatment in accordance with one representative embodiment.

FIG. 7 is a schematic block diagram illustrating another embodiment of a method 700 for diagnosing an exhaust aftertreatment in accordance with one representative embodiment. The method 700 begins and determines 702 an engine output power parameter for the engine 20 and determines 704 if the engine output power parameter is below an output power threshold. If the method 700 determines 704 that the engine output power parameter is not below the output power threshold, the method 700 returns and again determines 702 an engine output power parameter. If the method 700 determines 704 that the engine output power parameter is below the output power threshold, the method determines 706 a $NO_x$ efficiency of the SCR system 150. The method 700 determines 708 if the $NO_x$ efficiency is below a $NO_x$ efficiency threshold 312. If the method 700 determines 708 that the $NO_x$ efficiency is not below a $NO_x$ efficiency threshold 312, the method 700 returns and again determines 602 an engine output power parameter.

If the method 700 determines 708 that the $NO_x$ efficiency is below a $NO_x$ efficiency threshold 312, determines 710 an amount of change in the $NO_x$ efficiency within a sampling window. The method 700 determines 712 if the amount of change in the $NO_x$ efficiency exceeds a $NO_x$ efficiency change threshold 320. If the method 700 determines 712 that the amount of change in the $NO_x$ efficiency does not exceed a $NO_x$ efficiency change threshold 320, the method 700 returns and again determines 702 an engine output power parameter. If the method 700 determines 712 that the amount of change in the $NO_x$ efficiency exceeds the $NO_x$ efficiency change threshold 320, the method 700 sends 714 a $NO_x$ alarm signal and limits 716 the engine 20 to a low output, and the method 700 ends. One or more of the engine output module 402, the output power threshold module 404, the $NO_x$ module 406, the $NO_x$ threshold module 408, the $NO_x$ warning module 410, the $NO_x$ change module 502, the $NO_x$ change threshold module 504, and the disable module 506 may be employed to perform the steps of the method 700.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. An apparatus comprising:
an engine output module that determines an engine output power parameter, the engine output power parameter for an engine;
an output power threshold module that determines if the engine output power parameter is below an output power threshold;
a $NO_x$ module that determines a nitrogen oxide ("$NO_x$") efficiency of a selective catalytic reduction ("SCR") system in response to the output power threshold module determining that the determined engine output power parameter is below the output power threshold, the SCR system being in exhaust receiving communication with the engine;
a $NO_x$ threshold module that determines if the $NO_x$ efficiency is below a $NO_x$ efficiency threshold;
a $NO_x$ warning module that sends a $NO_x$ alarm signal in response to the $NO_x$ threshold module determining that the $NO_x$ efficiency is below the $NO_x$ efficiency threshold;
a $NO_x$ change module that determines an amount of change in the $NO_x$ efficiency within a sampling window; and
a $NO_x$ change threshold module that determines if the amount of change in the $NO_x$ efficiency determined by the $NO_x$ change module exceeds a $NO_x$ efficiency change threshold,
wherein the $NO_x$ warning module sends the $NO_x$ alarm signal in response to the $NO_x$ threshold module determining that the $NO_x$ efficiency is below the $NO_x$ efficiency threshold and the $NO_x$ change threshold module determining that the amount of change in the $NO_x$ efficiency exceeds the $NO_x$ efficiency change threshold.

2. The apparatus of claim 1, wherein the $NO_x$ module determines the $NO_x$ efficiency while the determined engine output power parameter is within an engine output power range, the engine output power range comprising a range below the output power threshold, and the $NO_x$ change threshold module determines if the amount of change in the $NO_x$ efficiency exceeds the $NO_x$ efficiency change threshold using $NO_x$ efficiency determinations taken while the engine output power parameter is within the engine output power range.

3. The apparatus of claim 1, wherein the sampling window comprises one of a window of time and a number of consecutive samples.

4. The apparatus of claim 1, wherein the engine output power parameter comprises a level of exhaust flow of the engine and the output power threshold comprises an engine exhaust level threshold.

5. The apparatus of claim 4, wherein the engine exhaust level threshold comprises an engine exhaust flow level that is below 50 percent of a maximum exhaust flow level.

6. The apparatus of claim 1, wherein one or more of:
the engine output power parameter comprises revolutions per minute ("RPM") of the engine and the output power threshold comprises an RPM threshold;
the engine output power parameter comprises an engine power output level of the engine and the output power threshold comprises a level of engine power output;
the engine output power parameter comprises a temperature of the engine and the output power threshold comprises a temperature threshold; and
the engine output power parameter comprises torque of the engine and the output power threshold comprises a torque threshold.

7. The apparatus of claim 1, wherein the determined engine output power parameter comprises an exponential weighted moving average of the determined engine output power parameter.

8. The apparatus of claim 1, wherein the engine output module determines the engine output power parameter in conjunction with a reductant tank refill event.

9. The apparatus of claim 1, wherein the engine output module determines the engine output power parameter at a sampling rate.

10. The apparatus of claim 9, wherein the engine output module determines the engine output power parameter at the sampling rate during a period that the engine is operating within a set of engine operating parameters.

11. The apparatus of claim 1, further comprising a disable module that limits the engine to a low output in response to receiving the $NO_x$ alarm signal.

12. The apparatus of claim 1, wherein the $NO_x$ alarm signal comprises a code that provides an indication of a diluted reductant.

13. A method comprising:
determining, by a controller communicably coupled to a selective catalytic reduction ("SCR") system and an engine, an engine output power parameter, the engine output power parameter for the engine;
determining, by the controller, if the engine output power parameter is below an output power threshold;
determining, by the controller, a nitrogen oxide ("$NO_x$") efficiency of the SCR a selective catalytic reduction ("SCR") system in response to determining that the engine output power parameter is below the output power threshold, the SCR system being in exhaust receiving communication with the engine;
determining, by the controller, if the $NO_x$ efficiency is below a $NO_x$ efficiency threshold;
determining an amount of change in the $NO_x$ efficiency within a sampling window;
determining if the amount of change in the $NO_x$ efficiency exceeds a $NO_x$ efficiency change threshold; and
sending, by the controller, a $NO_x$ alarm signal in response to determining that the $NO_x$ efficiency is below the $NO_x$ efficiency threshold,
wherein sending the $NO_x$ alarm signal is in response to determining that the $NO_x$ efficiency is below the $NO_x$ efficiency threshold and determining that the amount of change in the $NO_x$ efficiency exceeds the $NO_x$ efficiency change threshold.

14. The method of claim 13, wherein determining the $NO_x$ efficiency comprises determining the $NO_x$ efficiency while the engine output power parameter is within an engine output power range, the engine output power range comprising a range below the output power threshold, and determining if the amount of change in the $NO_x$ efficiency exceeds the $NO_x$ efficiency change threshold uses $NO_x$ efficiency determinations taken while the engine output power parameter is within the engine output power range.

15. The method of claim 13, wherein the engine output power parameter comprises a level of exhaust flow of the engine and the output power threshold comprises an engine exhaust level threshold.

16. An apparatus comprising:
an engine output module that determines an engine output power parameter, the engine output power parameter for an engine;
an output power threshold module that determines if the engine output power parameter is below an output power threshold;

a NOx module that determines a nitrogen oxide ("NOx") efficiency of a selective catalytic reduction ("SCR") system in response to the output power threshold module determining that the determined engine output power parameter is below the output power threshold, the SCR system being in exhaust receiving communication with the engine;

a NOx threshold module that determines if the NOx efficiency is below a NOx efficiency threshold; and a NOx warning module that sends a NOx alarm signal in response to the NOx threshold module determining that the NOx efficiency is below the NOx efficiency threshold, wherein one or more of:
- the engine output power parameter comprises revolutions per minute ("RPM") of the engine and the output power threshold comprises an RPM threshold;
- the engine output power parameter comprises an engine power output level of the engine and the output power threshold comprises a level of engine power output;
- the engine output power parameter comprises a temperature of the engine and the output power threshold comprises a temperature threshold; and
- the engine output power parameter comprises torque of the engine and the output power threshold comprises a torque threshold.

* * * * *